United States Patent
Bell et al.

(10) Patent No.: US 7,850,675 B2
(45) Date of Patent: Dec. 14, 2010

(54) REINFORCED VENOUS ACCESS CATHETER

(75) Inventors: Barbara Bell, Sudbury, MA (US); George Bourne, Southborough, MA (US); Raymond Lareau, Westford, MA (US); Kristian DiMatteo, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1450 days.

(21) Appl. No.: 10/894,992

(22) Filed: Jul. 20, 2004

(65) Prior Publication Data
US 2006/0020256 A1 Jan. 26, 2006

(51) Int. Cl.
*A61M 25/00* (2006.01)
(52) U.S. Cl. ............... 604/523; 604/524; 604/526
(58) Field of Classification Search .......... 604/523, 604/526, 524
See application file for complete search history.

(56) References Cited

U.S. PATENT DOCUMENTS

| | | | |
|---|---|---|---|
| 4,840,623 A | 6/1989 | Quackenbush | |
| 4,906,244 A * | 3/1990 | Pinchuk et al. | 606/194 |
| 5,462,523 A | 10/1995 | Samson et al. | |
| 5,879,499 A * | 3/1999 | Corvi | 156/175 |
| 5,928,216 A | 7/1999 | Spencer | |
| 6,127,320 A | 10/2000 | van Ooij et al. | |
| 6,171,295 B1 | 1/2001 | Garabedian et al. | |
| 6,213,995 B1 | 4/2001 | Steen et al. | |
| 6,663,614 B1 | 12/2003 | Carter | |
| 6,719,773 B1 * | 4/2004 | Boucher et al. | 606/192 |
| 2003/0114803 A1 | 6/2003 | Lerner | |

FOREIGN PATENT DOCUMENTS

| | | |
|---|---|---|
| EP | 0188041 | 7/1986 |
| EP | 0420993 | 4/1991 |
| WO | 00/03756 | 1/2000 |
| WO | 02/085227 | 10/2002 |
| WO | 2004/050144 | 6/2004 |

* cited by examiner

*Primary Examiner*—Nicholas D Lucchesi
*Assistant Examiner*—Quynh-Nhu H Vu
(74) *Attorney, Agent, or Firm*—Fay, Kaplun & Marcin, LLP

(57) ABSTRACT

A catheter for medical procedures comprises a shaft portion having a distal end insertable into a body lumen, the shaft portion having a wall defining a working lumen extending therewithin and a first strengthening element coupled to the wall to increase a burst pressure of the shaft portion, wherein the first strengthening element cooperates with a base material of the wall to define a flexible region of the shaft portion allowing the shaft portion to be atraumatically inserted into the body lumen.

53 Claims, 2 Drawing Sheets

REINFORCED VENOUS ACCESS CATHETER

BACKGROUND OF THE INVENTION

The treatment of chronic disease often requires repeated and prolonged access to a patient's vascular system to, e.g., to administer medications, blood products, nutrients and other fluids and/or to withdraw blood. When such procedures must be frequently repeated, it may be impractical and/or dangerous to insert and remove the catheter and the needle for each session. In this case, a semi-permanent catheter, (e.g., a peripherally inserted central catheter (PICC)), may be used. As would be understood by those skilled in the art, a PICC is a catheter that is inserted in a vein at a peripheral location, such as the arm or leg and threaded through the vein to the chest, in proximity to the heart.

To simplify the insertion process and reduce patient discomfort, PICCs and other semi-permanent catheters are generally made small and thin. Accordingly, their structural strength is limited by the thickness and type of material forming the catheter's walls. The amount of pressure and flow rate that the catheter can support without damage is also limited. If the maximum pressure the catheter can withstand (the burst pressure) or the maximum flow rate is exceeded, the catheter may be damaged or may completely fail possibly spilling fluids from the catheter into the body. During high pressure injections, escaping fluid may also damage the surrounding tissues.

Modern medical procedures rely considerably on visualization techniques to diagnose and treat diverse conditions. Some of these techniques include the injection of a contrast media to the vascular system to improve visualization of blood vessels and other biological structures during fluoroscopy, radiology, or other imaging. The contrast media is generally a liquid that is opaque to the visualization method used, so that body lumens containing the media appear distinct from other tissues. Typically, contrast media is introduced using a separate catheter designed to withstand the high injection pressures and flow rates necessary to disperse the media throughout the organs of interest. For example in the case of fluoroscopy, the contrast media may be a substance opaque to X-ray radiation. More modern visualization methods such as, for example, enhanced computed tomography (CT) may require the introduction of different contrast media, as would be understood by those skilled in the art.

Conventional PICC catheters are unable to withstand the high pressures and flow rates associated with the introduction of visualization media which are often substantially above what is used for the infusion of medications. Thus, it is often necessary to insert one or more additional catheters dedicated to the contrast media increasing patient discomfort and the time and costs associated with the procedure. If the patient exhibits poor peripheral venous access, the insertion of an additional contrast media catheter may be difficult.

SUMMARY OF THE INVENTION

In one aspect, the present invention is directed to a catheter for medical procedures comprising a shaft portion having a distal end insertable into a body lumen, the shaft portion including a wall defining a working lumen extending therewithin and a first strengthening element coupled to the wall to increase a burst pressure of the shaft portion, wherein the first strengthening element cooperates with a base material of the wall to define a flexible region of the shaft portion allowing the shaft portion to be atraumatically inserted into the body lumen.

DETAILED DESCRIPTION

Figures 1, 2, 3, 4:
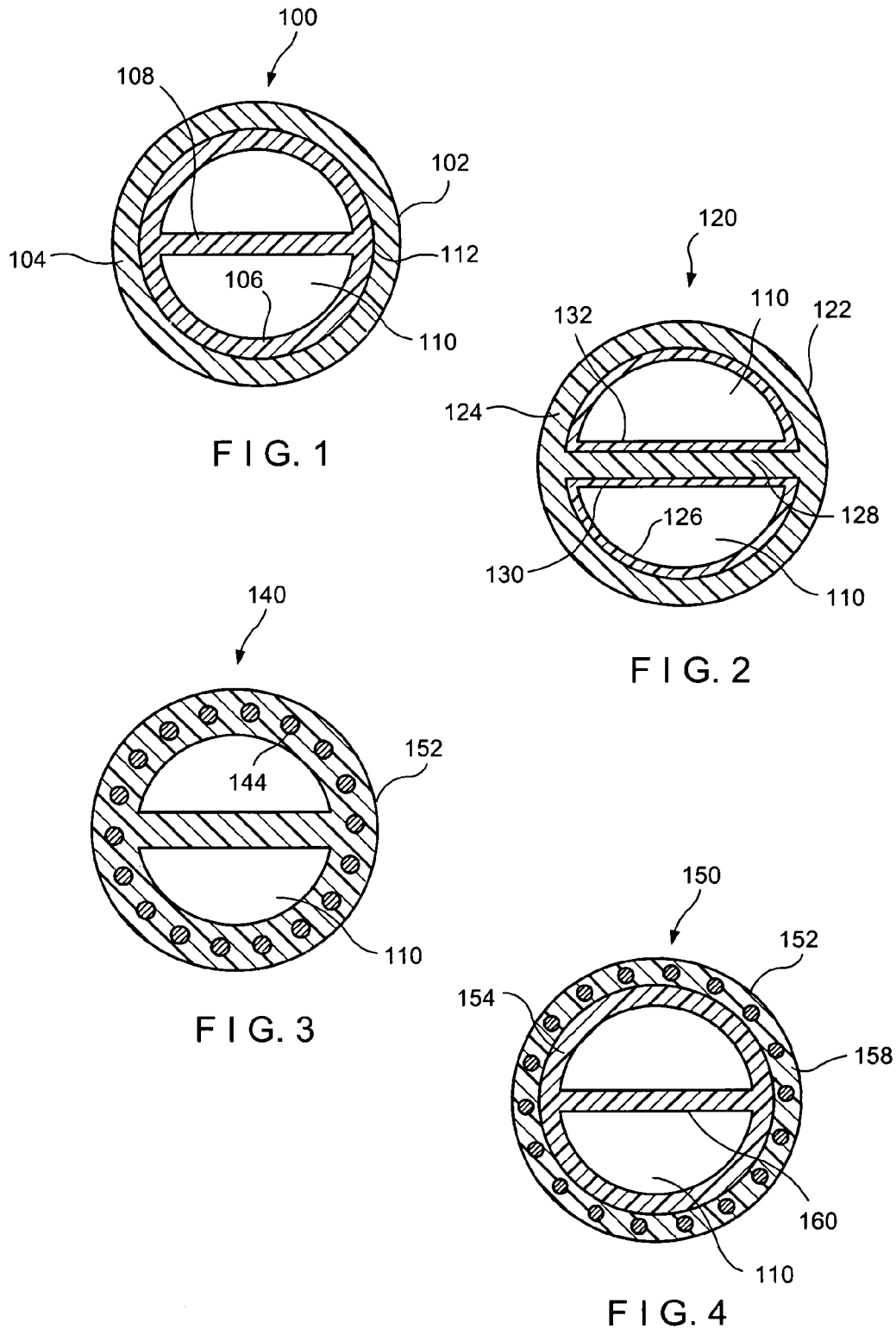
FIG. 1 is a cross sectional view showing a first embodiment of a venous access catheter with layered materials, according to the present invention.
FIG. 2 is a cross sectional view showing a second embodiment of a venous catheter with layered materials, according to the present invention.
FIG. 3 is a cross sectional view showing a third embodiment of a venous catheter with a braid, according to the present invention.
FIG. 4 is a cross sectional view showing a further embodiment of a venous catheter having a braid and layered materials, according to the present invention.

The present invention may be further understood with reference to the following description and the appended drawings, wherein like elements are referred to with the same reference numerals. The invention is related to medical devices used to introduce a contrast media fluid into a patient, preferably at high pressure and with a large flow rate. Specifically, the devices according to the invention may be used to inject the contrast media using a PICC.

As described above, where repeated access to the vascular system is required, a semi-permanent central venous catheter may be inserted in a vein kept in place for up to two years. A PICC typically comprises a flexible elongated portion tunneled from a remote peripheral location (an arm or leg) to a location near the heart. The proximal end of the PICC may be accessed via a port placed, for example, subcutaneously in the arm or chest of the patient or which may remain outside of the body.

As would be understood by those skilled in the art, the pressure exerted by the fluid is a function of the flow rate, the viscosity and the cross sectional flow area of the catheter, among other variables. Accordingly, limitations on the fluid pressure and/or flow rate are often specified for various types of catheters to ensure that the catheter will not be damaged during use by excessive strains. However as mentioned above, modern imaging methods often rely on the introduction of contrast fluids at high flow rates.

The catheter according to the present invention, may be used for both central venous access and the injection of contrast media decreasing patient discomfort and the time and expense of procedures. The catheter according to this invention, e.g., a PICC venous catheter, is at least partially reinforced to enhance its burst pressure and maximum flow rate to levels suitable for the introduction of contrast media without compromising kink resistance or increasing the cross sectional profile of the catheter, as compared to conventional PICC devices.

For example, a catheter according to the present invention will withstand a flow rate of about 4 to about 6 cc/sec and a pressure of more than about 300 PSI typical of power injection devices. A reinforcement is included in the exemplary catheter according to the invention to increase the burst pressure. In one embodiment, both the shaft of the catheter and an extension tube thereof are reinforced, to give a substantially uniform resistance to the increased pressure. Alternatively, only the shaft may be reinforced.

FIG. 1 shows an exemplary embodiment of a catheter comprising a reinforced portion in accord with the present invention. The exemplary catheter 100 is a dual lumen catheter in which the lumens 110 are separated by a partition 108 extending along a longitudinal axis of the catheter 100. In the exemplary embodiment, the catheter 100 has a layered construction, in which layers of stronger material are formed near layers of more flexible material to obtain desired mechanical characteristics of an outer wall 102. For example, an outer layer 104 of a material having a lower durometer value may be used, to retain the flexibility of a conventional catheter. Materials such as members of the polyurethane family that are alcohol compatible may be used advantageously in this function. An inner portion 106 of the catheter shaft wall 102 may be made of a material with a higher durometer value, to give strength to the composite assembly. For example, high strength thermoplastic polyurethanes, polyether block-amides and polyolefines may be used.

It is often necessary, in the course of a catheterization procedure, to adjust the length of the portion of the catheter inserted into the patient. Generally, the surgeon cuts a distal portion of the catheter to a desired length. Thus, in the case of a catheter 100 reinforced according to the present invention, the reinforcing material is preferably selected so that it can be easily cut with a blade. The exemplary materials described above fall within this category, so that the reinforced catheter 100 may be cut to a desired length using conventional methods. Alternatively, a material that is more difficult to cut may be used and/or a portion of the catheter 100 may be left unreinforced so that it may be cut. For example, the weakest portions of the catheter, such as the portion immediately distal to the suture wing, may be reinforced, leaving a 20-40 cm section of the tip of the catheter unreinforced. Because the portion immediately distal to the suture wing is one of the weakest and most likely to fail, reinforcement around the weak areas will prevent most failures from occurring. The unreinforced section of the catheter will continue to permit surgeons to easily cut the catheter in conventional manners, such as with a blade.

According to the present embodiment, the catheter 100 may be composed of various layers with each layer being formed of a material of different hardness, thereby allowing the catheter 100 to be atraumaticly inserted while exhibiting an improved resistance to the pressures associated with high flow rate power injection. As would be understood by those skilled in the art, the manufacture of the catheter 100 may be accomplished using a co-extrusion or a lamination process. For example, the softer, more flexible outer layer 104 of the shaft wall 102 may be co-extruded with the stiffer, higher durometer inner layer 106. This configuration provides both the flexible outer portion and the pressure resistant inner portion of the catheter 100.

The co-extrusion process may be carried out with polymers that are either compatible or non-compatible with one another. If non compatible polymers are used, it may be necessary to provide an intermediate tie layer along an interface 112 between the outer layer 104 and the inner layer 106. In this exemplary embodiment, a soft thermoplastic polyurethane (TPU) may be used for the outer layer 104 while a stiff polyester block-amide (PEBA), a stiff polyether block-amide, polyolefin or polytetrafluoroethylene (PTFE) may be used for the inner layer 106. The outer TPU exhibits softening while within the body, giving the desired flexibility, etc., and allowing atraumatic insertion. However the PEBA of the inner layer 106 retains its inherent strength and resistance to pressure.

FIG. 2 shows a second embodiment of the catheter 120 according to the invention. In this exemplary embodiment, the shaft wall 122 is reinforced by an inner layer 126 of a material with greater durometer values. Here, instead of an entire inner portion of the shaft 120 formed of a higher durometer material as in the example of FIG. 1, both the inner layer 126 and the outer layer 124 are formed of lower durometer, more flexible material. Specifically, the outer layer 124 of the wall 122 as well as the inner core 132 of a lumen divider 128 are formed from one piece of the lower durometer material. To this basic catheter shaft is then added a coating of higher durometer material on the inner sides of the two lumens 110, forming the inner layer 126 of the wall 122 as well as outer portions 130 of the divider 128. This embodiment provides for a flexible outer surface of the catheter 120, together with increased mechanical reinforcement of the stiffer lining of the dual lumens 110. Alternatively, the inner layers 126, 130 may be part of a separate tube of smaller diameter which is inserted into, but not bonded to the shaft of the catheter 120.

A further exemplary embodiment of a catheter shaft according to the invention is shown in FIG. 3. In this case, the increased resistance to fluid pressure within the lumens 110 is provided by a braid included therewithin. As shown, the catheter 140 includes an outer wall 142 comprising a braid 144, shown here in cross section. The braid 144 may be formed of any of a variety of materials, depending on the amount of additional pressure resistance desired. The braid 144 may be formed, for example, of a metal or alloy such as Nitinol or stainless steel. A material having shape memory properties may be especially well suited for reinforcement braids used in extension tubes of the catheter. In use, the proximal ends of these catheters are clamped shut between uses. Thus, the reinforcing braid will preferably be selected so that it will not retain the clamped shape, but will return to the original tubular shape when the clamping force is released. As would be understood by those skilled in the art, for catheters which are to be used in conjunction with MRI, the braid 144 is preferably formed of a non-ferro-magnetic material, for example, kevlar, vectran, silk, members of the polyolefin family and other types of polymer or other suitable material.

A variation of the braid reinforcement is shown in cross section in FIG. 4. The exemplary embodiment shown there comprises a braid 154 together with a dual material layered construction of the wall 152. The catheter shaft 150 includes two lumens with an inner portion 156 of the wall 152 formed of a material having an increased durometer with respect to a material comprising an outer portion 158 thereof. All of the variations in design described above with respect to the embodiments of FIGS. 1-3 may also be applied to the construction of the exemplary catheter shaft 150. It will be apparent to those of skill in the art that the radial location of the braid 154 within the wall 152 of the catheter shaft 150 may also be varied. It will also be apparent that the same reinforced construction methods described herein may be used for other components of a catheter, such as extension tubes, or for other medical tubes.

Figure 5:
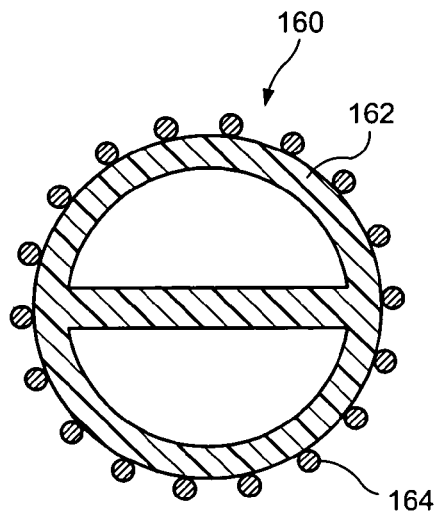
FIG. 5 is a cross sectional view showing another embodiment of a venous catheter having an externally placed braid.

In a different embodiment, the reinforcement braid may be disposed on the outside of the catheter body. For example, FIG. 5 shows a dual lumen catheter 160 having an outer wall 162 and a braid 164 disposed outside the surface of the wall 162. This configuration may provide manufacturing benefits compared to a configuration in which the braid 164 is embedded within the material of the catheter wall. For example, the braid 164 may be added to the assembly after the catheter has been formed by extrusion. The braid 164 may then be bonded to the catheter wall 162, or may be left free to slide longitudinally relative to the catheter. In this latter embodiment, the user may be allowed to longitudinally move the external braid to a desired position.

Figure 6:
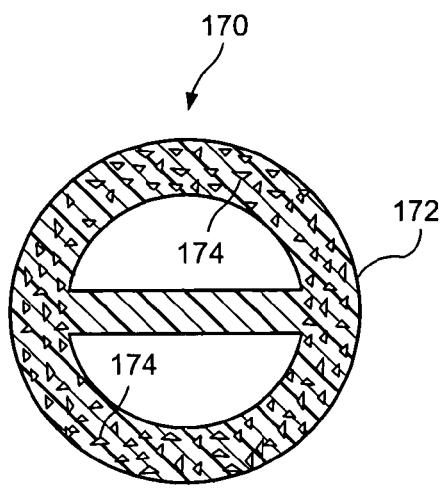
FIG. 6 is a cross sectional view showing a different embodiment of a venous catheter having a micro-particle reinforcement.

To further improve the pressure resistance and ultimate hoop strength of the base catheter material, micro particles may be added to the compound forming the catheter wall. The micro particles (sometimes referred to as nano-particles, depending on their size) may include clay and fumed silica. FIG. 6 shows an exemplary embodiment, in which a catheter shaft 170 is formed with a wall 172 comprising strengthening particles 174. The presence of the micro particles 174 increases the radial stiffness of the catheter wall 172, resulting in a more durable and more pressure resistant base material for the catheter. The distribution of the micro particles 174 both radially and longitudinally along the catheter 170 may be selected to obtain desired mechanical properties of the device. For example, a more pliable section of the catheter may be formed by locally reducing the amount of micro particles 174 added to the material of wall 172 while areas of increased stiffness may be created by increasing the amount of micro particles 174 in a region.

As an alternative to introducing strengthening particles into the catheter material, cross linking agents may be incorporated into the base material of the catheter shaft. For example, agents such as silanes, dicumyl peroxide, maleic anhydride and functionalized polymers may be added. These agents are effective in partially cross-linking thermoplastic polymers. Activation of the cross linking agents may be accomplished in a conventional manner, for example through secondary exposure to high energy sources such as electron beams to increase the strength of the base material. As indicated above, both the radial and tangential distribution of cross linking agents through the material of the catheter shaft may be selected to obtain desired mechanical properties, as would be understood by those skilled in the art.

Figure 7:
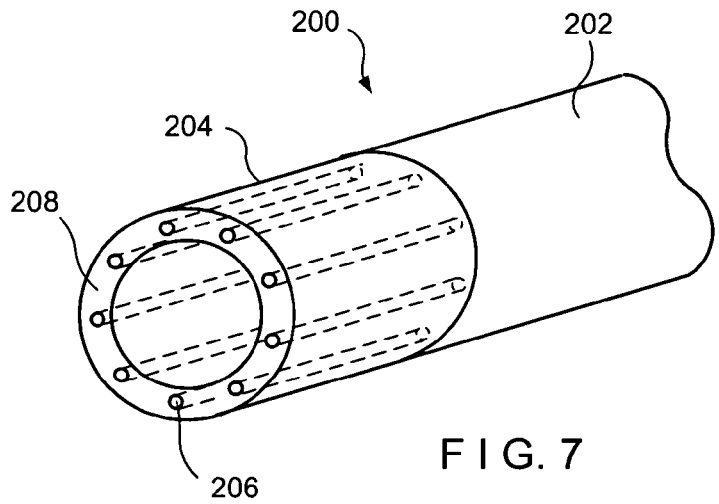
FIG. 7 is a perspective view showing a venous catheter partially reinforced according to the invention.

It will be apparent to those of skill in the art that the various methods described herein to increase the strength of a catheter shaft wall may be applied selectively to certain portions of the catheter in question. For example, FIG. 7 shows a catheter shaft 200 having a reinforced portion 204 and an unreinforced portion 202. The reinforced portion 204 may comprise any of the reinforcement elements or treatments described above, such as a mesh 206 embedded within wall 208 of the catheter shaft 200. It will be apparent to those of skill in the art that different types or combinations of reinforcements may be used, such as an external mesh, a layered multi-material composite structure, or the addition of reinforcing particles in the wall material. In the example depicted in FIG. 7, the shaft wall 208 is altered along its length, in the longitudinal direction. However, for different applications, the variation in structural reinforcement may be carried out in the angular direction or in the radial direction, as was described above. The non-uniform reinforcement construction may be applied to both catheter shaft and to the extension tubes, as needed.

In one exemplary application, the longitudinal variation in the strength of catheter wall 208 may be used to allow the user to trim the distal end of the catheter shaft 200, to provide a better fit in the patient. Leaving the unreinforced portion 202 without the reinforcement elements 206 included elsewhere (i.e., in reinforced portion 204) to increase pressure resistance allows the user to cut the wall 208 more easily. The reinforcement elements 206 may thus be selected to have greater strength, since it is not necessary that the user be able to cut therethrough to trim the catheter shaft 200 to the desired length. In one example, between about 15 cm and 20 cm of the distal end of catheter shaft 200 may form the unreinforced portion 202.

In another exemplary application, the wall of shaft 200 may be composed of varying materials, or may be otherwise reinforced by different amounts along its length to allow for increased strength and durability at specified stress points. These points of increased stress may occur during power injection of a fluid only at certain locations, such as near the injection point or near bends in the catheter. In this manner, the additional material used to strengthen the catheter may be targeted where it is most effective, without having to reinforce the entire catheter. This construction may be simpler and less costly than forming a catheter with reinforcements along its entire length.

Figure 8:
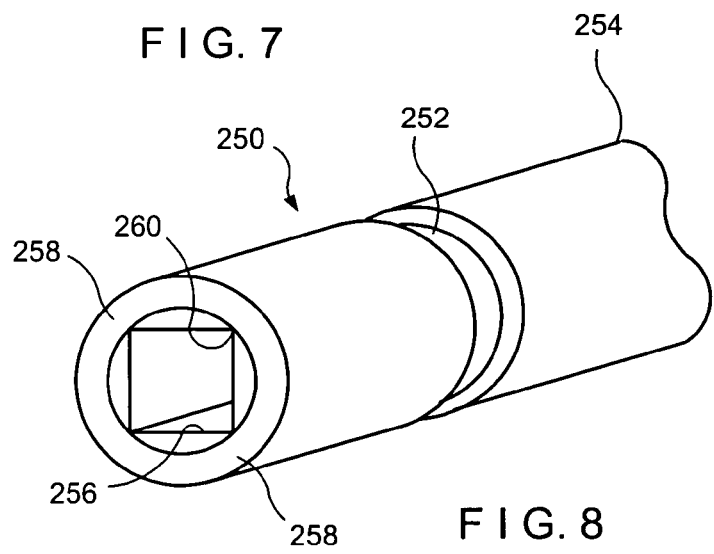
FIG. 8 is a perspective view showing a venous catheter with exemplary designed failure points.

According to another exemplary embodiment of the invention, the catheter shaft or the extension tube may be constructed with an inherent weak point designed to fail before the rest of the device does. When the catheter experiences excessive pressure, the extension tube will fail and release the pressure, leaving the catheter shaft intact. The extension tube may be formed with a tapered region of lesser strength, or by profiling the wall thickness of the tube to create the designated failure point. As shown in FIG. 8, a catheter extension tube 250 comprises a reduced thickness portion 252 in which the wall 254 is much thinner and is, at this point, able to withstand a pressure reduced with respect to the rest of the catheter. It will be apparent to those skilled in the art that the wall thickness reduction may be achieved by removing material from the outside of the wall (as shown), the inside of the wall or both.

In another embodiment, the inherent weak point may be formed by making either or both of the inside and outside diameters of the tube irregular in cross section. The non uniform wall thickness thus created, for example in the extension tube, defines specific sites for failure of the tube. As shown in the example of FIG. 8, a rectangular inner profile 256 of the extension tube 250 may be placed within a generally circular extension tube 250. This configuration may be used to define four thin walls 258 at the corners of the profile 256, which will tend to fail before thicker portions of the wall. In addition, the corners 260 act as stress concentrators, further ensuring that the extension tube 250 will fail at the location of the rectangular profile 256 when subject to excessive pressure. It will be apparent to those skilled in the art that the rectangular profile 256 may be used separately or in conjunction with the reduced thickness portion 252, as desired in specific applications.

The present invention has been described with reference to specific embodiments, and more specifically to a PICC catheter used for power injection of contrast media used in CT imaging. However, other embodiments may be devised that are applicable to other medical devices and procedures, without departing from the scope of the invention. Accordingly, various modifications and changes may be made to the embodiments, particularly with regard to dimensions and materials, without departing from the broadest spirit and scope of the present invention as set forth in the claims that follow. The specification and drawings are accordingly to be regarded in an illustrative rather than restrictive illustrative rather than restrictive sense.

What is claimed is:

1. A catheter for medical procedures comprising:
   a shaft portion having a distal end insertable into a body lumen, the shaft portion including a wall defining a working lumen extending therewithin; and a first strengthening element coupled to the wall increasing a burst pressure of the shaft portion, wherein the first strengthening element cooperates with a base material of the wall to define a flexible region of the shaft portion allowing the shaft to be atraumatically inserted into the body lumen, the wall being formed of a first layer of material having a durometer value greater than that of a material comprising a second layer of the wall wherein the first layer forms the first strengthening element and wherein an inner surface of the first layer defines an outer surface of the working lumen.

2. The catheter according to claim 1, wherein the first strengthening element comprises a braid forming a tubular shell around at least a portion of the working lumen.

3. The catheter according to claim 2, wherein the braid is embedded in the base material of the wall.

4. The catheter according to claim 2, wherein the braid is disposed around an outer surface of the wall.

5. The catheter according to claim 2, wherein the braid is made of metal.

6. The catheter according to claim 2, wherein the braid is made of stainless steel.

7. The catheter according to claim 2, wherein the braid is made of Nitinol.

8. The catheter according to claim 2, wherein the braid is made of a polymer material.

9. The catheter according to claim 2, wherein the braid is made of a polyolefin.

10. The catheter according to claim 2, wherein the braid is made of kevlar.

11. The catheter according to claim 2, wherein the braid is made of vectran.

12. The catheter according to claim 2, wherein the braid is made of silk.

13. The catheter of claim 1, wherein the wall comprises a reinforced portion and a non-reinforced portion separated from one another longitudinally along an axis of the shaft portion.

14. The catheter according to claim 1, wherein the second layer extends radially outward of the first layer.

15. The catheter according to claim 1, wherein the second layer comprises a thermoplastic polyurethane and the first layer comprises a polyether block amide.

16. The catheter according to claim 1, wherein the first and second layers are coextruded.

17. The catheter according to claim 1, wherein the first strengthening element comprises reinforcing particles dispersed within the base material of the wall.

18. The catheter according to claim 1, wherein the first strengthening element comprises cross linking agents incorporated in the base material for the wall and activated to strengthen the wall.

19. The catheter according to claim 1, further comprising an extension tube including a second strengthening element.

20. The catheter according to claim 1, wherein the first strengthening element is shorter than the shaft portion.

21. The catheter according to claim 1, wherein the burst pressure of the catheter is greater than 300 PSI.

22. The catheter according to claim 1, further comprising a designed failure point adapted to fail at a pressure below the burst pressure of the catheter.

23. The catheter according to claim 22, further comprising an extension tube, the designed failure point being disposed on the extension tube.

24. The catheter according to claim 22, wherein the failure point is a reduced thickness portion of the wall.

25. The catheter according to claim 22, wherein the failure point is defined by a region of irregular geometry of at least one of inner and outer cross sections of the wall.

26. A peripherally inserted central catheter comprising:
a shaft formed of a flexible base material, the shaft including a strengthening element raising a burst pressure of the shaft above a pressure generated during power injection, the strengthening element including a first layer of material having a durometer value higher than that of a material forming a second layer of the shaft, wherein an inner surface of the first layer defines an outer surface of a working lumen, the shaft further including a flexible portion allowing the shaft to be atraumatically navigated through a body lumen.

27. The central catheter according to claim 26, wherein the first and second layers are disposed radially relative to one another to form a wall of the shaft.

28. The central catheter according to claim 26, wherein the first layer is radially within the second layer.

29. The central catheter according to claim 28, wherein the first layer comprises a polyether block amide.

30. The central catheter according to claim 26, wherein the second layer defines the flexible portion.

31. The central catheter according to claim 30, wherein the second layer comprises a thermoplastic polyurethane.

32. The central catheter according to claim 26, wherein the strengthening element comprises a braid of material forming a tubular shell around a working lumen of the catheter.

33. The central catheter according to claim 32, wherein the braid is disposed on an outer surface of the shaft.

34. The central catheter according to claim 32, wherein the braid is formed of metal.

35. The central catheter according to claim 32, wherein the braid is formed of stainless steel.

36. The central catheter according to claim 32, wherein the braid is formed of Nitinol.

37. The central catheter according to claim 32, wherein the braid is formed of polymer material.

38. The central catheter according to claim 32, wherein the braid is formed of a polyolefin.

39. The central catheter according to claim 32, wherein the braid is formed of vectran.

40. The central catheter according to claim 32, wherein the braid is formed of silk.

41. The central catheter according to claim 32, wherein the braid extends along a proximal portion of the shaft.

42. The central catheter according to claim 32, wherein the braid is formed of silk.

43. The central catheter according to claim 32, wherein the braid extends along a proximal portion of the shaft.

44. The central catheter according to claim 26, wherein the strengthening element does not extend along the atraumatic portion.

45. The central catheter according to claim 26, wherein the strengthening element comprises micro particles added to the base material in selected regions.

46. The central catheter according to claim 45, wherein the micro particles comprise one of clay and fumed silica.

47. The central catheter according to claim 26, wherein the strengthening element comprises cross linking agents disposed within the base material and activated to strengthen the wall.

48. The central catheter according to claim 26, further comprising a designated failure point on one of the shaft and an extension tube of the catheter, the designated failure point being adapted to fail at a pressure less than a burst pressure of the rest of the catheter.

49. The central catheter according to claim 48, wherein the designated failure point comprises a reduced thickness portion of the wall.

50. The central catheter according to claim 48, wherein the designated failure point comprises a region of irregular cross section of the wall.

51. The central catheter according to claim 32, wherein the braid is embedded in the base material.

52. The central catheter according to claim 32, wherein the braid is formed of kevlar.

53. A peripherally inserted central catheter comprising:
a shaft formed of a flexible base material, the shaft including a strengthening element raising a burst pressure of the shaft above a pressure generated during power injection, the strengthening element including a first layer of material having a durometer value higher than that of a material forming a second layer of the shaft, wherein an inner surface of the first layer defines an outer surface of a working lumen, the shaft further including a flexible portion allowing the shaft to be atraumatically navigated through a body lumen, the atraumatic portion comprising a distal end of the shaft.

\* \* \* \* \*